United States Patent [19]

Sageser et al.

[11] Patent Number: 5,565,050

[45] Date of Patent: Oct. 15, 1996

[54] PROCESS FOR MAKING AN ABSORBENT ARTICLE HAVING INFLECTED BARRIER LEG CUFF

[75] Inventors: David M. Sageser; Stanley G. Juergens, both of Cincinnati; Mark D. Midkiff, Fairfield, all of Ohio

[73] Assignee: The Procter & Gamble Company, Cincinnati, Ohio

[21] Appl. No.: 467,741

[22] Filed: Jun. 6, 1995

Related U.S. Application Data

[62] Division of Ser. No. 260,638, Jun. 16, 1994, Pat. No. 5,496,428.

[51] Int. Cl.$^6$ .................................................... A61F 13/15
[52] U.S. Cl. .................. 156/73.1; 156/164; 156/204; 156/229; 156/267; 156/269; 156/291; 604/385.2
[58] Field of Search ............................. 604/385.1, 385.2; 156/204, 164, 229, 267, 73.1, 290, 291, 269

[56] References Cited

U.S. PATENT DOCUMENTS

| | | |
|---|---|---|
| Re. 26,151 | 1/1967 | Duncan et al. . |
| 3,180,335 | 4/1965 | Duncan et al. . |
| 3,776,233 | 12/1973 | Schaar . |
| 3,860,003 | 1/1975 | Buell . |
| 3,890,973 | 6/1975 | Davis et al. . |
| 3,911,173 | 10/1975 | Sprague, Jr. . |
| 3,929,134 | 12/1975 | Karami . |
| 3,929,135 | 12/1975 | Thompson . |
| 3,939,837 | 2/1976 | Taylor . |
| 4,040,423 | 8/1977 | Jones, Sr. . |
| 4,081,301 | 3/1978 | Buell . |
| 4,210,143 | 7/1980 | De Jonckheere . |
| 4,341,216 | 7/1982 | Obenour . |
| 4,342,314 | 8/1982 | Radel et al. . |
| 4,410,324 | 10/1983 | Sabee . |
| 4,463,045 | 7/1984 | Ahr et al. . |
| 4,515,595 | 5/1985 | Kievit et al. . |
| 4,573,986 | 4/1986 | Minetola et al. . |
| 4,610,678 | 9/1986 | Weisman et al. . |
| 4,657,539 | 4/1987 | Hasse . |
| 4,673,402 | 6/1987 | Weisman et al. . |
| 4,681,579 | 7/1987 | Toussant et al. . |
| 4,695,278 | 9/1987 | Lawson . |
| 4,704,115 | 11/1987 | Buell . |
| 4,704,116 | 11/1987 | Enloe . |

(List continued on next page.)

FOREIGN PATENT DOCUMENTS

| | | | |
|---|---|---|---|
| 374640 | 6/1990 | European Pat. Off. | ............ 604/385.2 |
| 518044 | 12/1992 | European Pat. Off. | ............ 604/385.2 |
| 614960 | 1/1994 | Japan | ............... 604/385.1 |
| 2160103 | 12/1985 | United Kingdom . | |
| 2161059 | 1/1986 | United Kingdom . | |
| 2197181 | 5/1988 | United Kingdom . | |
| 2196834 | 5/1988 | United Kingdom . | |
| 9207533 | 5/1992 | WIPO | ............... 604/385.2 |
| 9309739 | 5/1993 | WIPO | ............... 604/385.2 |
| WO93/14729 | 8/1993 | WIPO . | |
| WO9418927 | 10/1994 | WIPO . | |

*Primary Examiner*—Jeff H. Aftergut
*Attorney, Agent, or Firm*—Thompson Hine & Flory P.L.L.

[57] ABSTRACT

A process for making a wearable, absorbent article is described wherein two longitudinally extending barrier leg cuffs are attached to a chassis and the barrier leg cuffs are joined to the article so that they are directed inwardly toward a longitudinally extending centerline in the first waist region of the article and directed outwardly away from the longitudinally extending centerline in the second waist region of the article. The method describes the cuffs as being first attached in the first waist region and then in the second waist region in one embodiment and, in another embodiment, being attached in the second waist region first and then in the first waist region of the article. A process is also described for making a wearable, absorbent article wherein the barrier leg cuffs are attached to the article outboard of the longitudinally extending centerline in both the first waist and second waist regions of the article and wherein the barrier leg cuffs are joined partially to the article in the crotch region.

5 Claims, 6 Drawing Sheets

U.S. PATENT DOCUMENTS

| | | |
|---|---|---|
| 4,738,677 | 4/1988 | Foreman . |
| 4,795,452 | 1/1989 | Blaney et al. . |
| 4,795,454 | 1/1989 | Dragoo . |
| 4,808,178 | 2/1989 | Aziz et al. . |
| 4,822,435 | 4/1989 | Iguau et al. . |
| 4,834,735 | 5/1989 | Alemany et al. . |
| 4,834,740 | 5/1989 | Suzuki et al. . |
| 4,842,666 | 6/1989 | Werenicz . |
| 4,846,823 | 7/1989 | Enloe . |
| 4,846,825 | 7/1989 | Enloe et al. . |
| 4,850,989 | 7/1989 | Villez . |
| 4,888,231 | 12/1989 | Angstadt . |
| 4,900,317 | 2/1990 | Buell . |
| 4,900,384 | 2/1990 | Sanders ............... 604/385.2 X |
| 4,904,251 | 2/1990 | Igaue et al. . |
| 4,909,803 | 3/1990 | Aziz et al. . |
| 4,941,939 | 7/1990 | Nomura et al. . |
| 4,944,735 | 7/1990 | Mokry . |
| 4,964,860 | 10/1990 | Gipson et al. . |
| 5,021,051 | 6/1991 | Hiuke . |
| 5,024,672 | 6/1991 | Widland . |
| 5,030,303 | 7/1991 | Cucuzza ............... 604/385.2 X |
| 5,032,120 | 7/1991 | Freeland et al. . |
| 5,085,654 | 2/1992 | Buell . |
| 5,087,255 | 1/1992 | Sims . |
| 5,114,420 | 5/1992 | Igaue et al. . |
| 5,151,092 | 9/1992 | Buell et al. . |
| 5,167,653 | 12/1992 | Igaue et al. . |
| 5,190,606 | 3/1993 | Merkatoris et al. . |
| 5,217,455 | 8/1993 | Young et al. . |
| 5,241,431 | 9/1993 | Minetola et al. ............... 604/385.2 |
| 5,254,111 | 10/1993 | Cancio et al. . |
| 5,260,345 | 11/1993 | Des Marais et al. . |
| 5,275,590 | 1/1994 | Huffman et al. ............... 604/385.2 |
| 5,306,268 | 4/1994 | Enloe . |
| 5,318,544 | 6/1994 | Young et al. . |
| 5,403,301 | 4/1995 | Huffman et al. ............... 604/385.2 |
| B1 3,860,003 | 4/1989 | Buell . |

PROCESS FOR MAKING AN ABSORBENT ARTICLE HAVING INFLECTED BARRIER LEG CUFF

This is a divisional of application Ser. No. 08/260,638, filed Jun. 16, 1994 which is now U.S. Pat. No. 5,496,428.

FIELD OF THE INVENTION

The present invention relates to a method for making absorbent articles such as disposable diapers, and more particularly, to absorbent articles having barrier cuffs which improve the containment characteristics and fit of the absorbent article.

BACKGROUND OF THE INVENTION

The major function of absorbent articles such as disposable diapers and incontinent briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article and the absorbent article is not able to sustain a good fit on the wearer such that gaps are created allowing the exudates to leak out of the chassis of the absorbent article. For example, urine tends to be deposited onto the topsheet in gushes such that the urine migrates to the gaps in the chassis where it can come in contact with clothing or other articles and be absorbed by these articles. Additionally, loose fecal material that is not easily absorbed by the absorbent article tends to "float" on the liquid-receiving surface and work its way past the gaps in the article in the legs or waist of the wearer.

Contemporary disposable diapers have a topsheet, a backsheet, an absorbent core, and elasticized leg flaps generally formed from an elastic member being enclosed in the continuous topsheet and backsheet which extend beyond the edges of the absorbent core. These elasticized leg flaps prove efficient generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer to maintain a seal about the leg and minimize gapping. However, leakage along the perimeter of the diaper may still occur. As the diaper is worn for longer periods of time, forces tend to act on the diaper to degrade the initial fit on the wearer. Large gaps and sagging of the diaper in the legs and waist are formed by the degradation in fit. Thus, as liquids are deposited onto the topsheet, some of the liquid is not immediately absorbed through the topsheet and migrates toward the edges of the diaper where it can leak through or past the gaps in the diaper and come in contact with clothing or undergarments where it can be absorbed by and wicked into such garments.

Disposable diapers may be provided with barrier cuffs which inhibit loose fecal material or gushes of urine or liquids from soiling the wearer's clothing. The barrier cuffs restrain the free flow of this material and provide a structure to hold such material within the diaper so that as such material freely floats or flows on the topsheet of the diaper, it is contained within the diaper. Despite the effectiveness of such structures in containing such material, it has been found that liquids can leak beyond the barrier cuffs and soil the wearer's clothing because the diaper construction does not promote a sustained fit of the diaper on the wearer. Additionally, the barrier cuffs may not be properly applied to the wearer such that good initial fit is not achieved and the sustained fit is often worse.

SUMMARY OF THE INVENTION

This invention relates to an improved method for making a disposable absorbable article having an inflected barrier leg cuff This garment consists of a chassis which includes a topsheet, a backsheet and an absorbent core between the topsheet and the backsheet. The article further has a first waist region, a second waist region, and a crotch region located between the first and second waist regions.

In this method, barrier leg cuffs are attached to the topsheet of the article, one on each side of a longitudinal centerline. To allow for cutting of leg notches without interference from the barrier leg cuffs, the barrier cuffs are folded inwardly toward the longitudinal centerline of the article. After the leg notches are cut and removed, the barrier leg cuffs are attached in the second waist region directed outwardly from the longitudinal centerline. Next, the barrier leg cuffs are folded inwardly toward the longitudinal centerline and joined to the chassis at the first waist region of the article. Finally, the article is folded and then separated for packaging. This entire process can be carried out in one machine direction thus eliminating the need for changing machine direction or refeeding the article into the assembly line.

In a second embodiment of this invention, the barrier leg cuffs are first attached to the topsheet on each side of the longitudinal centerline. Next, the barrier leg cuffs are secured to the topsheet in the first waist region of the article so that they are directed inwardly toward the longitudinal centerline. Then the chassis is formed and the leg notches are cut forming ear panels in the first and second waist regions. Next, the ear panels in the second waist region are folded inwardly toward the longitudinal centerline and over the barrier leg cuffs to which the ear panels are joined. Finally, the article is cut to prepare it for shipment.

In a third embodiment of this invention, the barrier leg cuffs are first attached to the topsheet on each side of the longitudinal centerline. They are then attached at the second waist region of the article so that they are folded outwardly of the centerline. Next, the chassis is formed in any conventional manner. Once the chassis has been formed, the leg notches are cut. Then, a bonding agent is applied to the interior side of the distal portion of the barrier leg cuffs in the first waist region of the article. The article is folded and separated into separate articles. In a fourth embodiment of this invention, the barrier leg cuffs are first attached to the topsheet. They are secured in the first and second waist regions so that both leg cuffs are either directed outwardly of the centerline or inwardly toward the longitudinal centerline. After the barrier leg cuffs are secured in the first and second waist regions, they are partially secured in the crotch region to provide a stand up barrier in that region. The article is then folded and prepared for shipment.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

The Product

Figure 1:
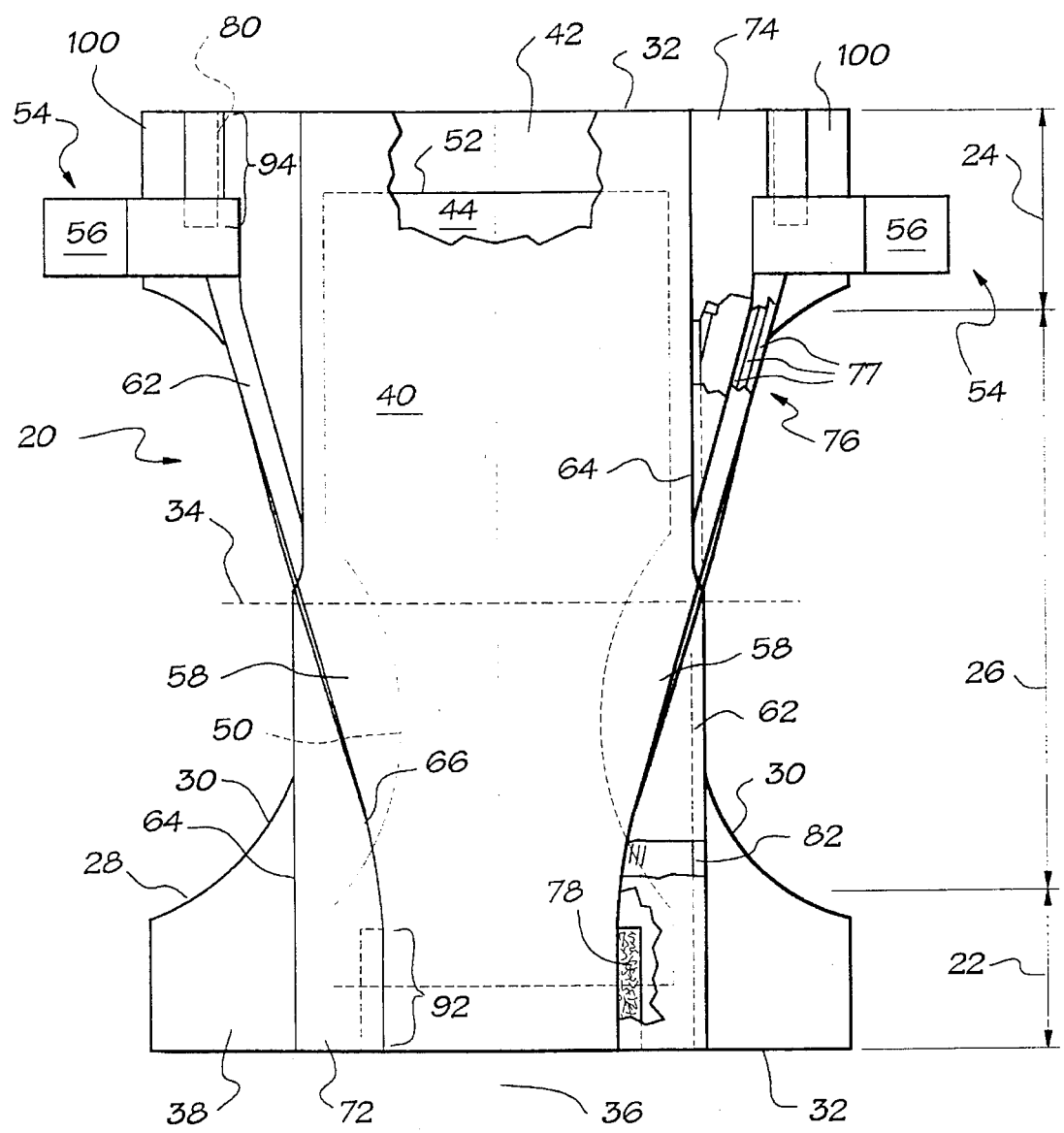
FIG. 1 is a plan view of the diaper made by the process of this invention.

As used herein, the term "absorbent article" refers to articles which absorb and contain body exudates and more specifically refers to articles which are placed against or in proximity to the body of the wearer to absorb and contain the various exudates discharged from the body. Absorbent articles are typically differentiated by whether they are reusable or disposable. Disposable absorbent articles are those articles which are intended to be discarded after a single use (i.e., they are not intended to be laundered or otherwise restored or reused). The absorbent articles of the present invention are preferably disposable absorbent articles. The absorbent articles may be further defined by whether they are "unitary" such that they do not require separate manipulative parts or whether they comprise an element of a diaper system such as a separate holder and liner. The absorbent articles of the present invention are preferably unitary. A preferred embodiment of a unitary disposable absorbent article of the present invention, diaper 20, is shown in FIG. 1. As used herein, the term "diaper" refers to a garment generally worn by infants and incontinent persons that is worn about the lower torso of the wearer. It should be understood, however, that the present invention is also applicable to other disposable absorbent articles such as incontinence briefs or undergarments, disposable training pants, diaper holders, sanitary napkins, and the like.

FIG. 1 is a plane view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer. The diaper 20 is shown in FIG. 1 to have a first waist region 22, a second waist region 24, a crotch region 26, and a periphery 28 which is defined by the outer edges of the diaper 20 in which the longitudinal edges are designated 30 and the end edges are designated 32. The diaper 20 additionally has a lateral centerline which is designated 34 and a longitudinal centerline which is designated 36.

The diaper 20 comprises a liquid pervious topsheet 38, the liquid-receiving surface of the diaper 20 being generally defined by the topsheet 38 and being designated 40; a liquid impervious backsheet 42; an absorbent core 44 having a garment surface 46, a body surface 48, and edges that are designated side edges 50 and waist edges 52; fastening means 54 for securing the diaper 20 on the wearer such as the pair of tape tab fasteners 56; a side flap 58 extending outwardly from each side edge 50 of the absorbent core 44 in at least the crotch region 26; ear flaps 100; barrier cuffs 62 each having a proximal edge 64, a distal edge 66, a first end 72, and a second end 74; spacing means 76 such as elastic members 77 for spacing the distal edge 66 away from the liquid-receiving surface 40; first closing means 78 for securing a portion of the distal edge 66 inboard of the proximal edge 64; and second closing means 80 for securing a portion of the distal edge 66 outboard of the proximal edge 64.

FIG. 1 shows an embodiment of the diaper 20 in which the backsheet 42 has length and width dimensions generally larger than those of the absorbent core 44. The backsheet 42 extends beyond the edges of the absorbent core 44 to thereby form the periphery 28 of the diaper 20. The periphery 28 defines the outer perimeter or, in other words, the edges of the diaper 20. The periphery 28 comprises the longitudinal edges 30 and the end edges 32. As shown in FIG. 1, the topsheet 38 is generally coterminous with the backsheet 42 along at least the end edges 32 and preferably the longitudinal edges 30.

The diaper 20 has a first waist region 22 and a second waist region 24 extending, respectively, from the end edges 32 of the diaper periphery 28 toward the lateral centerline 34 of the diaper 20 a distance up to about ⅓, preferably from about ⅛ to about ¼, of the length of the diaper 20. The waist regions 22 and 24 generally comprise those portions of the diaper 20 which, when worn, encircle the waist of the wearer. The crotch region 26 is that portion of the diaper 20 positioned between the first waist region 22 and the second waist region 24, and comprises that portion of the diaper 20 which, when worn, is positioned between the legs of the wearer and covers the lower torso of the wearer.

The absorbent core 44 may be any means which is generally compressible, conformable, non-irritating to the wearer's skin, and capable of absorbing and retaining liquids and certain body exudates. A preferred absorbent core 44 has a garment surface 46 and a body surface 48.

The absorbent core 44 may be manufactured in a wide variety of sizes and shapes (e.g., rectangular, hour-glass, asymmetric, etc.) and from a wide variety of liquid absorbent materials commonly used in disposable diapers and other absorbent articles, such as comminuted wood pulp which is generally referred to as air-felt. Examples of other suitable absorbent materials include creped cellulose wadding, absorbent foams, absorbent sponges, super absorbent polymers, absorbent gelling materials, or any equivalent materials or combination of materials. The total absorbent capacity of the absorbent core 44 should, however, be compatible with the design exudate loading in the intended use of the diaper 20. The size and absorbent capacity of the absorbent core 44 may be varied to accommodate wearers ranging from infants through adults.

The backsheet 42 is positioned adjacent the garment surface 46 of the absorbent core 44 and is preferably secured thereby by core attachment means (not shown) such as those well known in the art. For example, the backsheet 42 may be secured to the absorbent core 44 by a uniform continuous layer of adhesive, a patterned layer of adhesive, or an array of separate lines or spots of adhesive. The core attachment means preferably comprises an open pattern network of filaments of adhesive.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body. The backsheet 42 is preferably embossed and/or matte finished to provide a more clothlike appearance. The backsheet 42 may permit vapors to escape from the absorbent core 44 while still preventing exudates from passing through the backsheet 42. The size of the backsheet 42 is dictated by the size of the absorbent core 44 and the exact diaper design selected.

The topsheet 38 is compliant, soft feeling, and non-irritating to the wearer's skin. The topsheet 38 is liquid pervious permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g. polyester or polypropylene fibers) or from a combination of natural and synthetic fibers. Preferably, it is made of a hydrophobic material to isolate the wearer's skin from liquids in the absorbent core 44. If the topsheet 38 is made of a hydrophobic material, at least the upper surface of the topsheet 38 is treated to be hydrophilic so that liquids will transfer through the topsheet more rapidly. This diminishes the likelihood that body exudates will flow off the topsheet 38 rather than being drawn through the topsheet 38 and being absorbed by the absorbent core 44. The topsheet 38 can be rendered hydrophilic by treating it with a surfactant. Suitable methods for treating the topsheet 38 with a surfactant include spraying the topsheet 38 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The side flaps 58 are that portion of the diaper 20 between the periphery 28 and the side edges 50 of the absorbent core 44. Thus, in a preferred embodiment as shown in FIG. 1, the side flaps 58 are formed from the extension of the backsheet 42 and the topsheet 38 extending outwardly from and along the side edges 50 of the absorbent core 44 of the diaper 20 in at least the crotch region 26.

The diaper 20 is provided with a fastening means 54 for forming a side closure in the diaper 20. Thus, the diaper 20 is fitted to the wearer and preferably the first waist region 22 and the second waist region 24 are maintained in an overlapping configuration when the diaper 20 is worn. While the fastening means 54 may comprise any of a number of fastening systems as are known in the art such as belts or inner fastening members, in a preferred embodiment the fastening means 54 comprises a tape tab 56 disposed adjacent each longitudinal edge 30 of the diaper 20 preferably in the second waist region 24. Tape tab fasteners 54 are preferably applied to the second waist region 24 of the diaper 20 to provide a fastening means 54 to hold the diaper 20 to the wearer, although they may alternatively be disposed in the first waist region 22. The tape tab fasteners 54 can be any of those tape tabs well known in the art.

The barrier leg cuffs 62 provide a structure to restrain the free flow of body exudates along the liquid-receiving surface 40 and to hold and contain such exudates within the diaper 20 and to provide a gasketing action about the wearer. Each barrier cuff 62 is a flexible member having a proximal edge 64 and a distal edge 66. In addition, if the spacing means 76 comprises one or more elastic members 77, the barrier cuffs 62 must be contractible so that the distal edges 66 may be sufficiently spaced away from the liquid-receiving surface 40 to form a channel and may provide a gasketing action about the buttocks of the wearer. The barrier cuffs 62 may be manufactured from a wide variety of materials such as polypropylene, polyester, rayon, nylon, foams, plastic films, formed films, elastic laminates and elastic foams. A number of manufacturing techniques may be used to manufacture the barrier cuffs. For example, the barrier cuffs 62 may be woven, non-woven, spunbonded, carded, or the like. A particularly preferred barrier cuff 62 comprises a laminate of a non-woven polypropylene material secured to a liquid impermeable polyethylene film. The materials may be secured or laminated to each other by any methods as is known in the art.

The barrier cuff 62, and more particularly, the proximal edge 64, is disposed adjacent to and preferably inboard of the longitudinal edge 30 of the diaper 20. The term "inboard" is defined as the direction toward the centerline (34 or 36, respectively) of the diaper 20 that is parallel to the respective edge of the diaper 20 along which the particular barrier cuff is disposed. The proximal edge 64 is preferably disposed inboard of the longitudinal edge 30 so that exudates, especially loose fecal material which is not easily absorbed and tends to float along the liquid-receiving surface 40, will contact the barrier cuff 62 before it can contact the edges of the diaper 20. Thus, the proximal edge 64 is preferably disposed between the longitudinal edge 30 and the longitudinal centerline 36 of the diaper 20. Most preferably, the proximal edge 64 is disposed between the longitudinal edge 30 and the side edge 50 of the absorbent core 44 in at least the crotch region 26 of the diaper 20. (It should be noted that if the side flaps 58 are elasticized by one or more flap elastic members to form a gasketing cuff adjacent each longitudinal edge 30, as is known in the art, then the proximal edge 64 is preferably positioned between the innermost flap elastic member and the side edge 50 of the absorbent core 44 in at least the crotch region 26.)

The proximal edges 64 and the distal edges 66 are in a spaced relation to each other and define the effective width of each of the barrier cuffs 62. The proximal edges 64 and the distal edges 66 may be in a parallel, nonparallel, rectilinear or curvilinear relationship. In addition, each of the barrier cuffs 62 may have a variety of different cross-sectional areas including circular, square, rectangular, or any other shape. Preferably, the proximal edge 64 is spaced from the distal edge 66 in a parallel and rectilinear relationship. The effective width of the barrier cuff 62 is an important parameter in reducing leakage of body exudates out of the diaper 20. If the effective width of the barrier cuff 62 is too small, then gaps will be formed between the leg of the wearer and the distal edge 66 such that liquids may flow over the distal edge 66 to the periphery 28 of the diaper 20. The effective width should be dimensionalized as the size of the wearer increases or decreases, particularly with adult wearers.

The distal edge 66 of each barrier cuff 62 is preferably not secured to any underlying elements of the diaper 20 in at least the crotch region 26 so that it may be spaced away from the liquid-receiving surface 40. The distal edge 66 is preferably spaced away from the liquid-receiving surface 40 so that the barrier cuff 62 may form a channel to enhance the containment of the diaper 20. As used herein, "spaced" includes embodiments wherein the distal edges 66 may assume one or more positions relative to the liquid-receiving surface 40 including at some times assuming a position adjacent the liquid-receiving surface 40.

The distal edge 66 of each barrier cuff 62 is preferably disposed inboard of the proximal edge 64 in the first waist region 22 so as to present a more effective barrier against the flow of exudates. The distal edges 66 may also be disposed outboard of the of the proximal edge 64 in the first waist region 22. The distal edges 66 are maintained inboard of the proximal edges 64 in the first waist region 22 by the first closing means 78 so as to obviate their inversion. The first closing means 78 is located in a first closure zone 92 which is disposed inboard of the side flaps 58 and, in the same embodiment, or in another preferred embodiment, at least a portion of the first closing means 78 is positioned above at least a portion of the absorbent core 44.

As shown in FIG. 1, the distal edges 66 are preferably laterally spaced apart from each other in the first waist region 22. However, the lateral spacing between the distal edges 66 can range from being crossed over each other to abutting each other to being laterally spaced apart up to the width of the proximal edges in the first waist region 22. Thus, in the embodiment shown in FIG. 1, the distal edges 66 may be laterally spaced apart from about −25 mm (−1 inch) (overlapping edges) up to about 150 mm (6 inches). Preferably, the distal edges 66 are spaced apart so that the barrier cuff 62 will fit in the innermost leg crease of the wearer rather than ride along the wearer's outer thigh.

The distal edges 66 are also shown in FIG. 1 to be disposed parallel to each other and perpendicular to the end edge 32 of the diaper 20 in the first waist region 22. While this is a preferred embodiment, the distal edges 66 may alternatively be angled toward or away from each other, preferably toward each other, such that the distal edges 66 are disposed non-perpendicular to the end edges 32. Angling the barrier cuffs relative to the end edge 32 may assist in allowing the barrier cuff to remain spaced from the liquid-receiving surface 40 in the crotch region 26 during use.

The distal edges 66 are laterally spaced apart from each other in the crotch region 26. The lateral spacing of the distal edges 66 is especially important in the crotch region 26 to prevent body exudates, especially urine, from leaking out of the diaper 20 in the leg regions of the wearer. If the distal edges 66 are laterally spaced too far from each other, then the barrier cuffs 62 have an increased tendency to "flip out" in the crotch region 26 such that urine can flow over the barrier cuffs 62. If the distal edges 66 are spaced too close to each other, then the barrier cuffs 62 provide a reduced area for deposition of exudates such that exudates could be deposited directly onto the barrier cuffs 62 and flow to the edges of the diaper 20.

The distal edge 66 of each barrier cuff 62 is disposed outboard of each proximal edge 64 in the second waist region 24 of the diaper 20. The term "outboard" is defined as the direction away from the longitudinal centerline 36 of the diaper 20 that is parallel to the respective edge of the diaper 20 along which the barrier cuff 62 is disposed, (i.e., the direction opposite from the direction defined by the term "inboard"). Thus, the barrier cuff 62 is "flipped out" in the second waist region 24. The flipped out portion of the barrier cuff 62 promotes better containment that is less sensitive to application variations and provides a contoured fit about the buttocks of the wearer. The distal edges 66 may be maintained outboard of the proximal edges 64 in the second waist region 24 by the second closing means 80. One skilled in the art will appreciate that the distal edges 66 may also be disposed inboard of the proximal edges 64 in the second waist region 24.

As shown in FIG. 1, the distal edges 66 are laterally spaced apart from each other in the second waist region 24. However, the spacing between the distal edges 66 can range such that the distal edges 66 are angled relative to each other. The distal edges 66 are also shown in FIG. 1 to be disposed parallel to each other and perpendicular to the end edge 32 of the diaper 20. The distal edges 66 may alternatively be angled toward or away from each other, preferably away from each other, such that the distal edges 66 are disposed non-perpendicularly to the end edges 32.

Because the distal edge 66 is disposed inboard of the proximal edge 64 in the first waist region 22 and outboard of the proximal edge 64 in the second waist region 24, the distal edge 66 is inflected ("flipped out") along its length. Thus, the article fits the contours of the wearer's body. This inflection transitions the barrier cuff 62 from snugly fitting about the buttocks (the flipped out portion) to fitting in the "no motion" zone of the legs for better containment (the stand-up portion; i.e., the distal edge 66 being disposed inboard of the proximal edge 64). The resultant inflected barrier cuff 62 is easier to apply to the wearer and ensures that the fit of the barrier cuff 62 is in the "no motion" zone in the crotch region 26 with a snug fit about the wearer's buttocks in at least the second waist region 24.

It has been found that the inflected barrier cuff 62 thus provides both a gasketing action about the buttocks of the wearer to provide a snug fit which reduces leakage of body exudates, especially runny bowel movement, and a stand-up barrier cuff 62 in the crotch region 26 and the first waist region 22 to constrain, contain and hold body exudates within the diaper 22 along the channel (not shown). However, it has been found that if the barrier cuff 62 is "flipped out" too far toward the first waist region 22 along the length of the barrier cuff 62, then body exudates will tend to flow over the barrier cuffs. Thus, it is preferred that the inflected barrier cuffs 62, in use, provide a gasketing action about the buttocks of the wearer to provide a snug fit (i.e., the flipped out portion of the barrier cuffs is positioned) in less than about 50% of the length of the diaper, more preferably less than about 40% of the length of the diaper 20, and most preferably only in the second waist region 24. (The percent length of the flipped out portion is defined as that length of the diaper in which the barrier cuff is flipped out divided by the total length of the diaper times 100%). Thus, the stand-up portion of the barrier cuff (distal edge 66 disposed inboard of the proximal edge 64) is provided, in use, in at least about 50% of the length of the diaper, preferably at least about 60% of the length of the diaper, and most preferably from the first waist region 22 to and throughout the crotch region 26.

The flipped out portion of the barrier cuff 62 can be maintained in less than about 50% of the length of the diaper 20 in a number of different ways. For example, the second closure zone 94 is preferably longer than the first closure zone 92. Alternatively, a closure attachment means may be positioned on the barrier cuff 62 toward or in the crotch region 26 of the diaper for securing the distal edge 66 inboard of the proximal edge 64 so that the flipped out portion is maintained in less than about 50% of the length.

A channel (not shown) is formed between the proximal edge 64 and the distal edge 66 of the barrier cuff 62 in the crotch region 26 and the first waist region 22. The channel forms a barrier to the flow of exudates as they tend to move or float across the topsheet 38. The channel also contains and holds exudates within the diaper 20 until the diaper 20 can be removed.

In another embodiment of the diaper 20, the distal edges 66 of the barrier leg cuffs 62 may be disposed outboard of the proximal edge 64 in both the first and second waist regions 22 and 24. The leg cuffs 62 are partially secured inward of the proximal edge 64 in the crotch region 26. In this embodiment, the lower half of the leg cuff 62 is attached to the topsheet by those methods discussed above. The distal edge 66 in the crotch region 26 is then moved to a position approximately perpendicular to the topsheet 38 by action of the elastic members 77. This embodiment provides a gasketing action in both the first and second waist regions 22 and 24 and a stand up barrier in the crotch region 26.

In another embodiment of the alternate embodiment, the distal edges 66 of the barrier leg cuffs 62 may either be disposed inboard of the proximal edge 64 in both the first and second waist regions 22 and 24 or both disposed outboard of the proximal edge 64 in both waist regions 22 and 24. The leg cuffs 62 are partially secured inward of the proximal edge 64 in the crotch region 26. In this embodiment, the lower half of the leg cuff 62 is attached to the topsheet in the crotch region 26 by those methods discussed above. The distal edge 66 in the crotch region 26 is then moved to a position approximately perpendicular to the topsheet 38 by action of the elastic members 77. This embodiment provides a gasketing action in both the first and second waist regions 22 and 24 and a stand up barrier in the crotch region 26.

The barrier cuffs 62 are preferably liquid impermeable so as to prevent the strikethrough of body exudates. A liquid impermeable barrier cuff 62 retards the movement of liquid through the barrier cuff 62, thereby making it more leakage resistant. The barrier cuffs 62 may be rendered liquid impermeable in any manner well known in the art such as selectively treating the barrier cuffs or by choosing a liquid impermeable material, such as a hydrophobic nonwoven material, for the barrier cuffs 62.

The barrier cuffs 62 may additionally be provided with absorbent means secured to or within the barrier cuff 62. The absorbent means absorb and contain exudates which contact the barrier cuff 62. The absorbent means may be any means which is capable of absorbing and retaining liquids and may have any size, shape, configuration or absorbent capacity. The absorbent means may be disposed in the barrier cuff 62 along the inboard surfaces of the barrier cuff 62 or within the barrier cuff 62.

A spacing means 76 for spacing the distal edge 66 away from the liquid-receiving surface 40 is any member which gathers, contracts, stiffens, shortens or otherwise acts on the barrier cuff 62 so as to cause the barrier cuffs 62 to stand up to provide a channel along the barrier cuff 62 that acts as a constraint against the leakage of exudates and a gasketing action about the buttocks of the wearer to provide a snug fit.

As shown in FIG. 1, the spacing means 76 preferably comprises elastic members 77 operatively associated with each of the barrier cuffs 62 adjacent the distal edge 66. The elastic members 77 are preferably secured to the barrier cuff 62 in an elastically contractible condition so that in a normally unrestrained configuration, the elastic members 77 effectively contract or gather the distal edge 66 of the barrier cuff 62. The elastic members 77 can be secured to the barrier cuff 62 in an elastically contractible condition in at least two ways as is discussed in U.S. Pat. No. 3,860,003 entitled "Contractible Side Portion For Disposable Diaper" which issued to Kenneth B. Buell on Jan. 26, 1974, which is incorporated by reference herein. In addition, the length of the elastic member 77 in general is dictated by the diaper design. In the embodiment illustrated in FIG. 1, the elastic member 77 extends along essentially the entire length of the barrier cuff 62 in the crotch region 26, although other lengths are cognizable.

The diaper 20 is preferably applied to a wearer by positioning the second waist region 24 behind the wearer's back and drawing the remainder of the diaper 20 between the wearer's leg so that the first waist region 22 is positioned across the front of the wearer. The ends of the tape tab fasteners 56 are then secured preferably to outwardly facing areas of the diaper 20. In this manner, the stand-up position of the barrier cuffs 62 should be disposed in the "no motion" zone of the wearer in the crotch region 26 and the flipped out portion be positioned in less than about 50% of the length of the diaper 20, preferably so as to be disposed in only the second waist region 24, so as to provide a gasketing action about the buttocks of the wearer.

The Process

Having described the product in detail, the process of this invention by which the product is manufactured shall be discussed.

In the first embodiment, the barrier leg cuffs 62 are joined to a completed chassis. The topsheet 38, absorbent core 44 and backsheet 42 are assembled into a chassis in any conventional fashion. The topsheet 38 and the backsheet 42 are associated together in any suitable manner as is well known in the diaper manufacturing art. As used herein, the term "associated" encompasses configurations whereby the topsheet 38 is directly joined to the backsheet 42 by affixing the topsheet 38 directly to the backsheet 42, and configurations whereby the topsheet 38 is indirectly joined to the backsheet 42 by affixing the topsheet 38 to intermediate members which in turn are affixed to the backsheet 42. The topsheet 38 and the backsheet 42 can be joined directly to each other in the diaper periphery 28 by flap attachment means (not shown) such as an adhesive or any other attachment means as is known in the art. Thus, for example, a uniform continuous layer of adhesive, a patterned layer of adhesive, an array of separate lines or spots of adhesive, or a network of adhesive filaments may be used.

Figure 2:
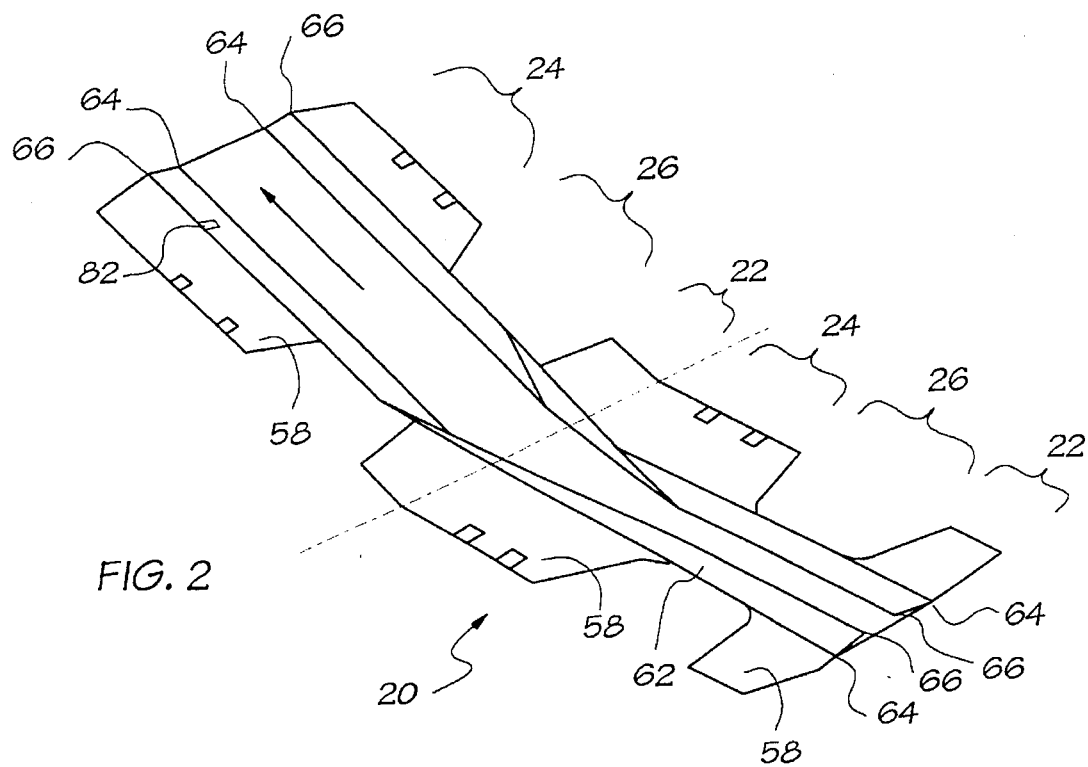
FIG. 2 presents an illustration of one embodiment of the process of this invention.

After the chassis has been formed, the barrier leg cuffs 62 are joined to the topsheet 38 of the completed chassis by their proximal edges 64 as shown in FIG. 2. The term "joined" includes any means for securing the barrier cuff 62 to the diaper 20, and includes embodiments wherein the barrier cuffs 62 are separate members directly or indirectly secured to the side flaps 58 (i.e., integral barrier cuffs) or embodiments wherein the barrier cuffs 62 are constructed from the same member or material as an element of the diaper 20 such as the side flap 58 so that the barrier cuffs 62 are a continuous and undivided element of the side flap 58 (i.e., unitary barrier cuffs). The barrier cuffs 62 may alternatively be joined to the backsheet 42, the topsheet 38, the absorbent core 44, or any combination of these or other elements of the diaper 20. The term "joined" includes any means for securing the barrier cuff 62 to the diaper 20, and includes embodiments wherein the barrier cuffs 62 are separate members directly or indirectly secured to the side flaps 58 (i.e., integral barrier cuffs) or embodiments wherein the barrier cuffs 62 are constructed from the same member or material as an element of the diaper 20 so that the barrier cuffs 62 are a continuous and undivided element of the diaper 20 (i.e., unitary barrier cuffs). The proximal edges 64 and topsheet 38 are joined together in any suitable manner. As used herein, the term "joined" encompasses configurations whereby the proximal edges 64 are directly secured to the topsheet 38 by affixing the proximal edges 64 directly to the side flap 58 and configurations whereby the proximal edges 64 are indirectly secured to the topsheet 38 by affixing the proximal edges 64 to intermediate members which in turn are affixed to the side flap 58. In the preferred embodiment, the proximal edges 64 and the topsheet 38 are directly secured to each other at least in the crotch region 26 by the seal means (not shown).

The seal means provides a seal along the proximal edge 64 to present a barrier to the wicking of liquids through the topsheet 38. While the topsheet 38 or the absorbent core 44 may extend beyond the seal means, protection against leakage of liquids emanating from the edges of the absorbent core 44 or wicking along the topsheet 38 may be enhanced by making the topsheet or the absorbent core not extend beyond the proximal edge 64. The seal means may be any means for securing the proximal edges 64 to the side flaps 58 such as adhesives, heat/pressure sealing, ultrasonic bonding, or any other means or methods as are known in the art. Exemplary adhesives are manufactured by Findley Adhesives, Inc. of Elmgrove, Wis. and marketed as Findley Adhesive 581 or by H. B. Fuller Company of St. Paul, Minn. and marketed as HM-1258.

As illustrated in FIG. 2, after the leg cuffs 62 are joined to the body of the diaper 20 along the cuffs' proximal edge 64, the cuffs 62 are positioned such that the elasticated (distal) edge 66 is oriented inwardly toward the longitudinal centerline 36 of the diaper 20. Once the elasticated edge 66 has been positioned inwardly toward the longitudinal centerline 36, leg notches (not shown) can be cut and removed without leg cuff interference.

Next, a bonding agent, as described above, is provided in the second waist region 24 and the cuffs 62 are attached outwardly of the longitudinal centerline and anchored to the diaper 20. The seal means 82 may be any means for securing the proximal edges 64 to the side flaps 58 such as adhesives, heat/pressure sealing, ultrasonic bonding, or any other means or methods as are known in the art. The seal means may be applied to either the side of the leg cuff 62 outboard of the longitudinal centerline 36 or to the side flaps 58. In either instance, once the cuffs 62 are folded outwardly, the cuffs 62 will become bonded to the diaper 20.

Figure 2A:
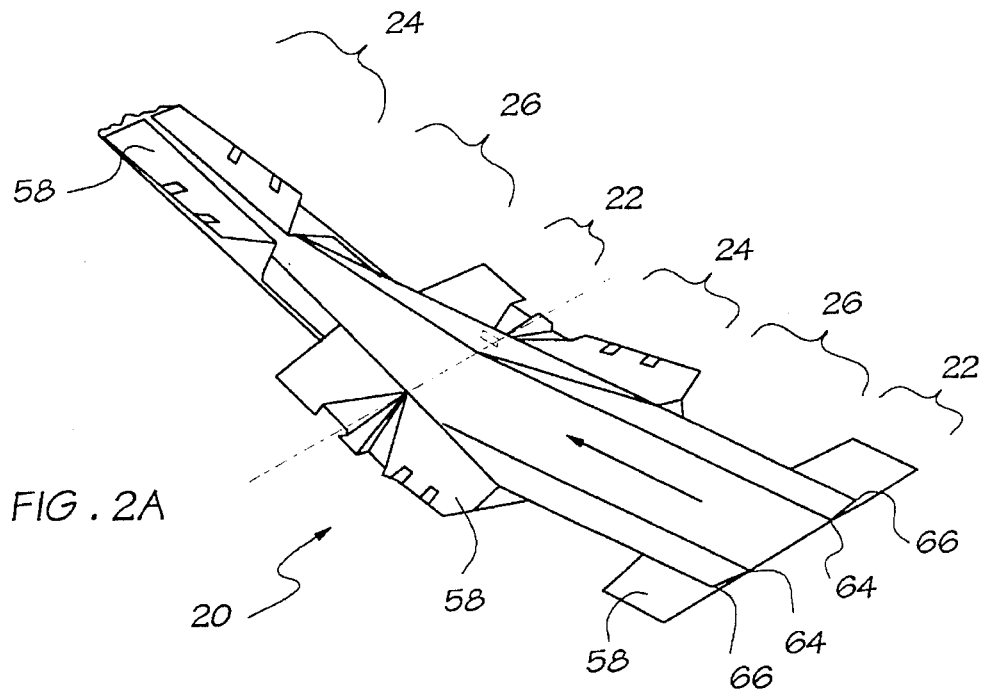
FIG. 2A presents a continuing illustration of the process presented in FIG. 2.

As shown in FIG. 2A, after the cuffs 62 are folded outwardly, an intermittent bond is applied in the first waist region 22 of the diaper 20 either on the side of the barrier leg cuff 62 inboard of the longitudinal centerline 36 or to the body of the diaper 20 itself. The bond may be any means commonly used in the art such as adhesives, heat/pressure sealing, ultrasonic bonding or any other means or method presently known. The method preferably used to bond the barrier leg cuff 62 to the first waist region 22 of the diaper 20 is an adhesive. Next, the diaper 20 is folded so that the barrier leg cuffs 62 become attached inwardly toward the longitudinal centerline 36 in the first waist region 22. Finally, the diapers 20 are separated from the web into individual articles and prepared for packaging. Typically, this performed by cutting the diapers 20 transversely.

Figure 3:
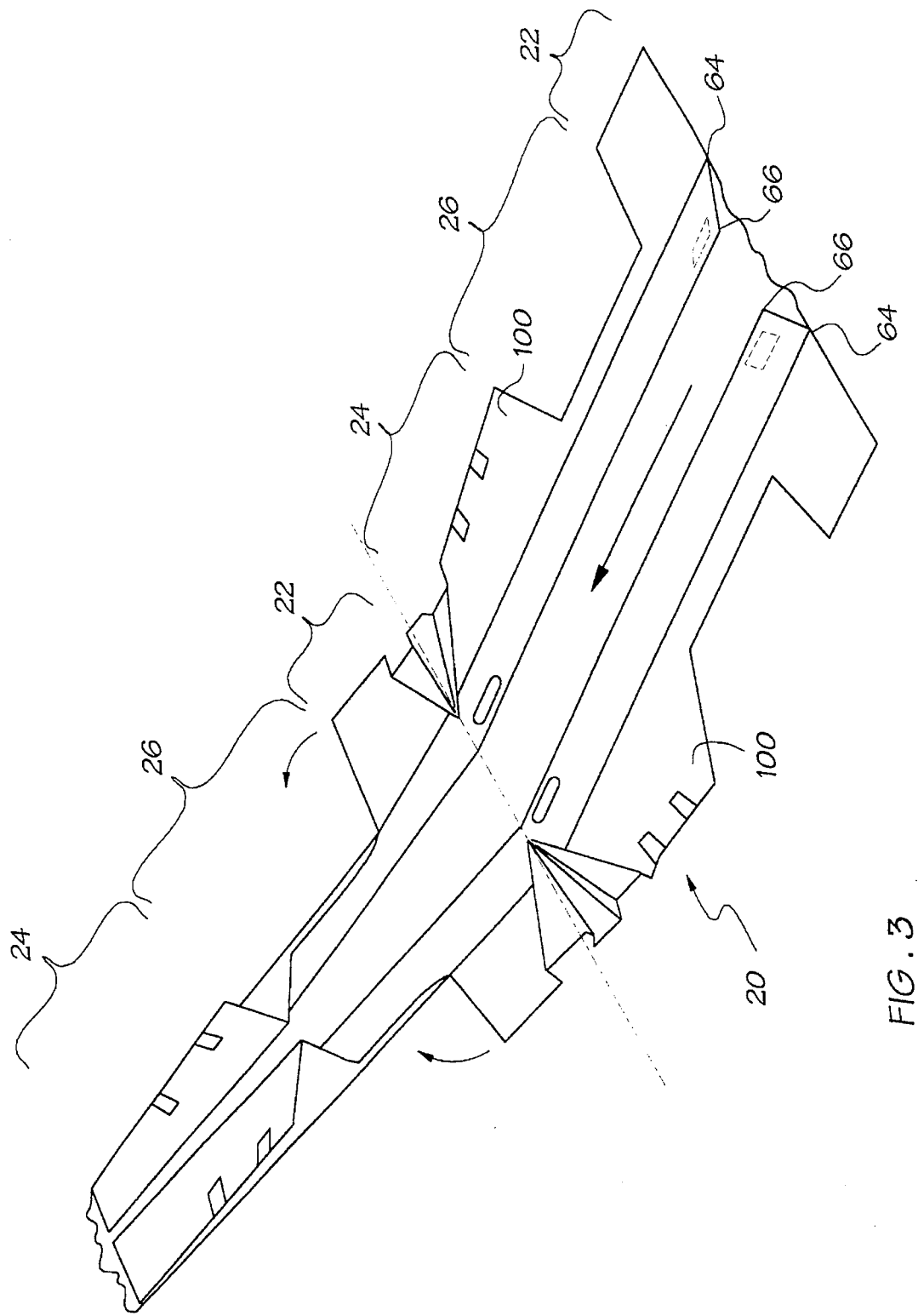
FIG. 3 presents an illustration of a second embodiment of the process of this invention.

As shown in FIG. 3, a Second embodiment, the barrier leg cuffs 62 are joined to the topsheet 38 by a continuous bond, as discussed previously. The barrier leg cuffs 62 are joined to the topsheet 38 with their respective distal edges 66 directed inwardly toward the longitudinal centerline 36 of the diaper 20. A bonding agent, as described above, is then provided in the first waist region 22 of the diaper 20. While the distal edges 66 are directed inwardly toward the longitudinal centerline 36, the distal edges 66 are anchored in the first waist region 22 of the diaper 20. This anchoring means can be any conventional means known in the an such as adhesives, heat/pressure sealing, ultrasonic bonding or any other means or methods known in the art. Again, the anchoring means may be applied to either the side of the leg cuff 62 inboard of the longitudinal centerline 36 or to the body of the diaper 20.

After the barrier leg cuffs 62 are bonded to the first waist region 22 of the topsheet 38, the topsheet 38 is then associated with a backsheet 42 and an absorbent core 44, in the manner described above, to form a chassis.

Once the topsheet, backsheet 42 and absorbent core 44 have been associated (not shown), leg notches are then cut forming ear panels 100 in at least the second waist region.

After the leg notches have been cut, a bonding agent is applied in the second waist region 24 of the diaper 20. The bonding agent can be applied either to the side of the barrier leg cuff 62 outboard of the longitudinal centerline 36 or to the topsheet 38 of the diaper 20 near the outboard side of the barrier leg cuff 62. The ear panels 100 are then folded inwardly toward the longitudinal centerline 36 onto the barrier leg cuffs 62. The bonding agent bonds the distal edge 66 to the ear panel 100 in the second waist region 24 to the barrier leg cuff 62. The diapers 20 are then separated into individual articles and prepared for packaging.

Figure 4:
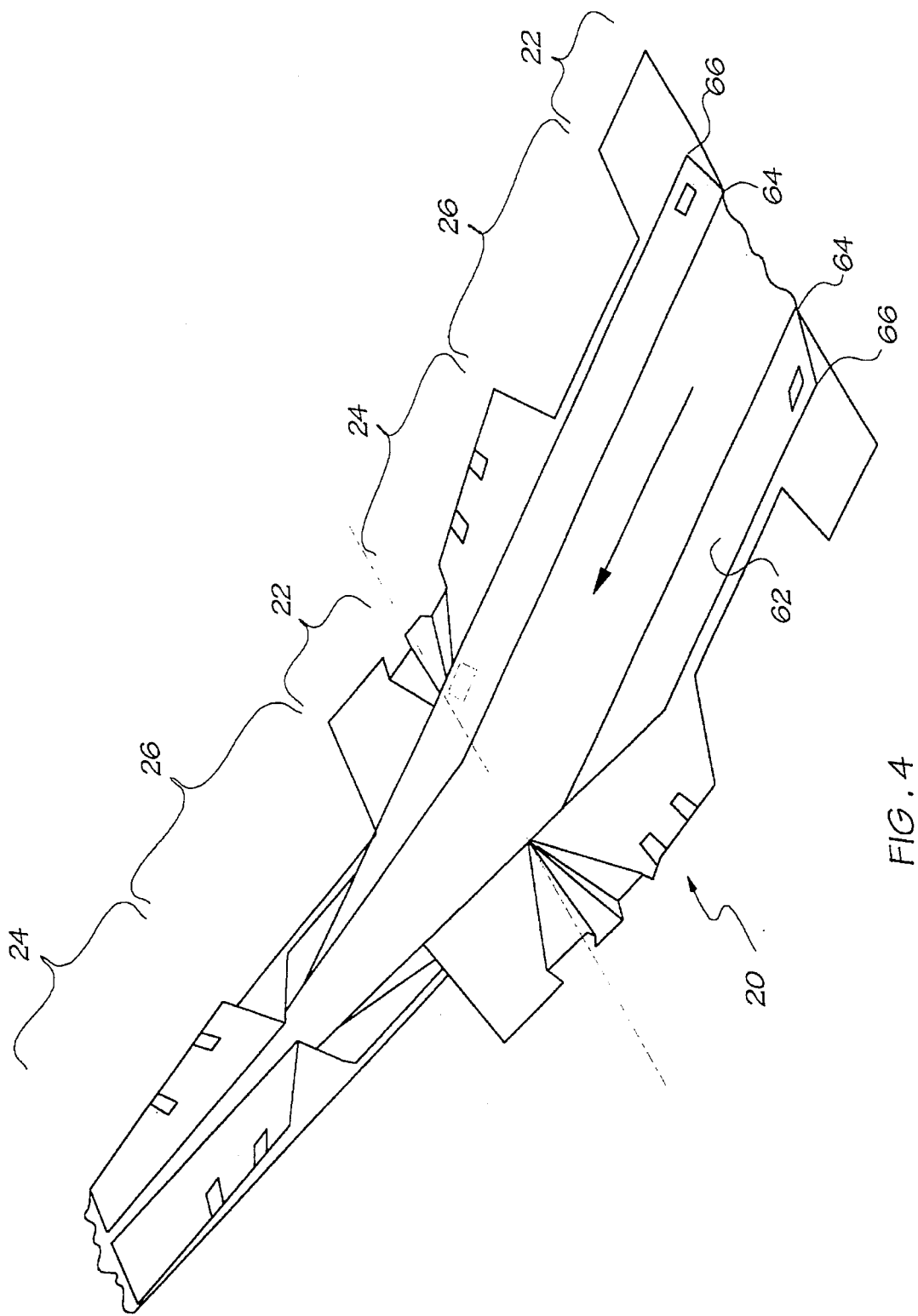
FIG. 4 presents an illustration of a third embodiment of the process of this invention.

As shown in FIG. 4, in a third embodiment, the barrier leg cuffs 62 are first associated with the topsheet 38. A bonding agent is then provided in the second waist region 24 and the barrier leg cuffs 62 are secured to the topsheet 38 with their distal edges 66 directed outwardly from the centerline 36 in the second waist region 24 of the diaper 20. The leg cuffs 62 are secured in the second waist region 24 of the diaper 20 by any conventional means such as adhesives, heat/pressure sealing ultrasonic bonding, or any other means or methods as are known in the art. The topsheet 38 is then associated with the backsheet 42 and the absorbent core 44 to form a chassis. Once the chassis has been formed, the leg notches are cut. After the leg notches have been cut, the bonding agent is provided in the first waist region 22 of the diaper 20 in this embodiment, the bonding agent is applied to either the side of the barrier leg cuff 62 inboard of the longitudinal centerline 36 or to the body of the diaper 20 near the inboard side of leg cuff 62 in the first waist region 22 of the diaper 20. Thus, when the diaper 20 is folded the front bond is secured. The sequence of the third embodiment differs from that which is described in the second embodiment in that the bond in the second waist region 24 is completed first. After the diaper 20 has been folded, the diapers 20 are then separated and prepared for packaging.

Figure 5:
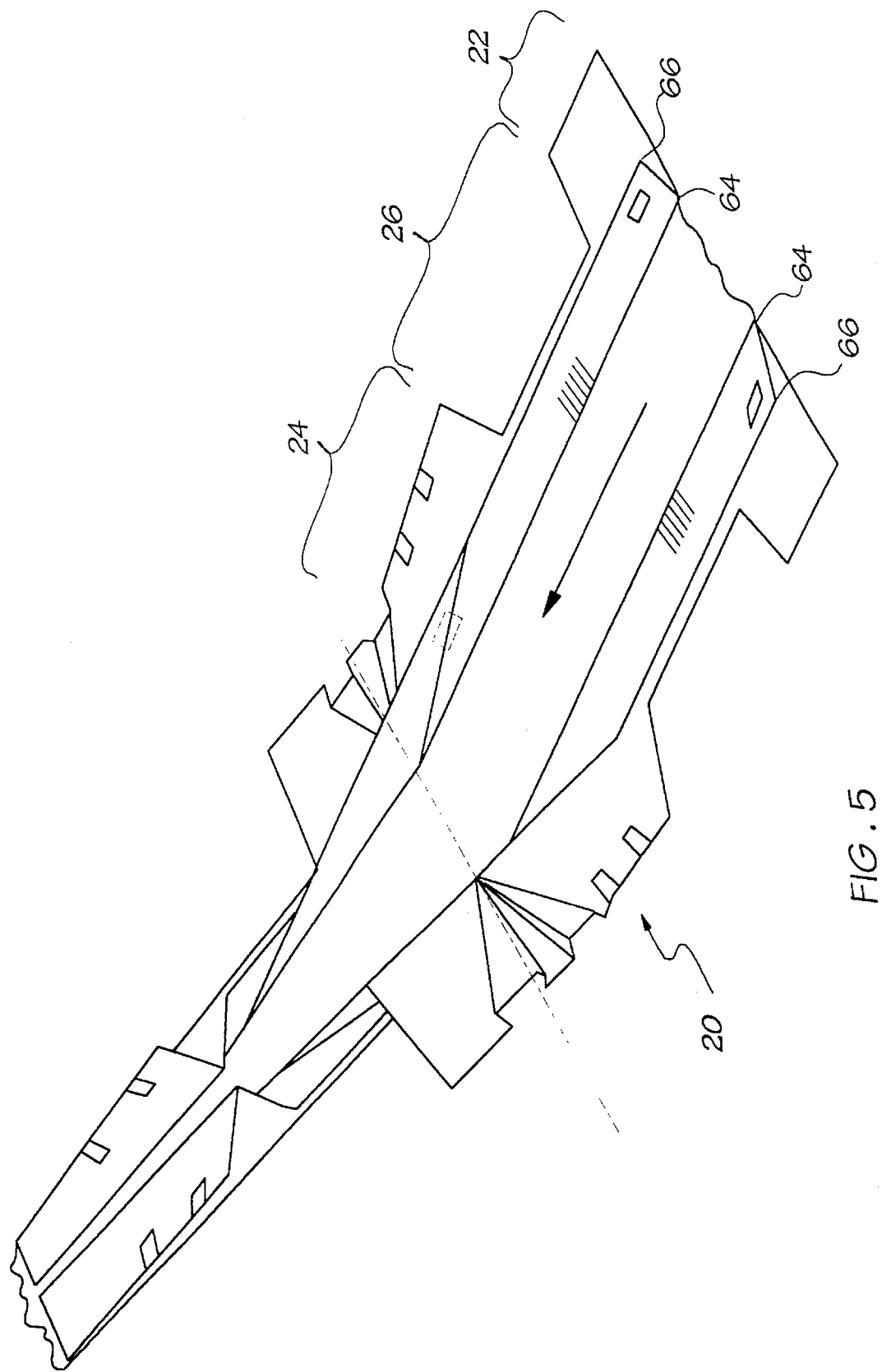
FIG. 5 presents an illustration of a fourth embodiment of the process of this invention.

In a fourth embodiment, shown in FIG. 5, the leg cuffs 62 are attached to the topsheet 38 with the distal edge 66 of each leg cuff 62 directed outwardly from the centerline 36 of the article 20. As the cuffs are being attached, the cuffs 62 are secured to the topsheet 38 outboard of the longitudinal centerline 36 in both the first and second waist regions 22 and 24. In an alternate embodiment of this embodiment, the leg cuffs 62 can be attached to the topsheet 38 with the distal edge 66 of each cuff 62 directed inwardly toward the centerline 36. The topsheet 38, absorbent core 44 and backsheet 42 are then assembled into a chassis in any conventional fashion, as described above. After the diaper 20 has been assembled, the leg notches are then cut. Next, an adhesive is provided on the proximal half of the inboard side of the barrier leg cuff 62 in the crotch region 26. The diaper 20 is then folded and cut transversely to its proper length. In this embodiment, when the diaper 20 is opened by the consumer, the leg cuffs 62 are partially joined to the topsheet 38 in the crotch region 26, i.e., they are secured to the topsheet from the proximal edge 64 to approximately half their height, and joined with their distal edges 66 directed outwardly of the longitudinal centerline 36 in both the first and second waist regions 22 and 24. When the alternate embodiment is opened, the leg cuffs 62 are direct inwardly toward the longitudinal centerline in both the first and second waist regions 22 and 24.

Figure 6:
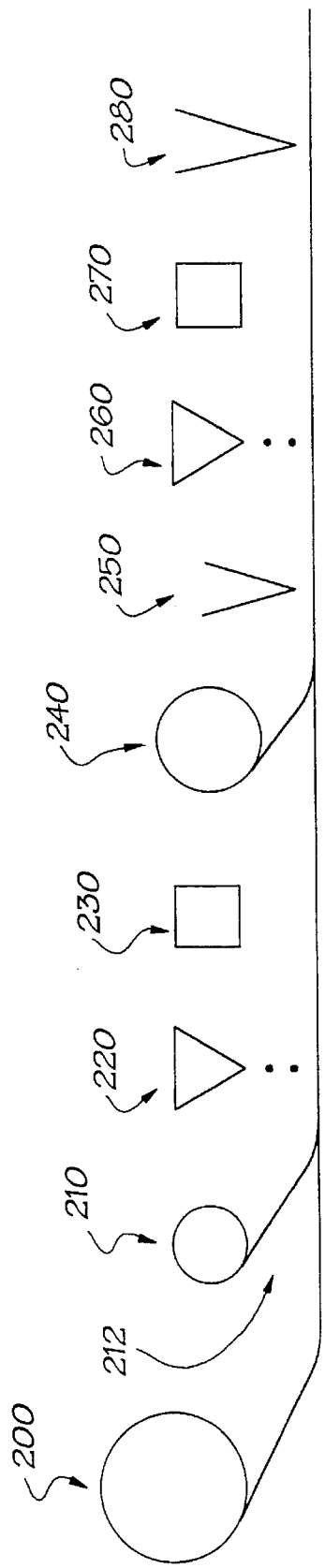
FIG. 6 presents a diagrammatic illustration of the basic process of this invention.

Having described the processes of this invention in detail, a general summary is provided in FIG. 6. FIG. 6 presents a schematic illustration of the process of this invention. One skilled in the art should note that slight variations occur in the various embodiments so that certain steps may or may not be included in each embodiment. The web 200 can be an assembled chassis, as illustrated in the process accompanying FIG. 2, a topsheet 38, as illustrated in the process accompanying FIGS. 3–5, or a back sheet 42. The web 212 of the leg cuffs 62 are attached to the web 200. The leg cuffs 62 can be attached either from a single web which is subsequently split into two separate webs to create each of the leg cuffs 62 or each of the leg cuffs 62 can be attached from a separate web of material. These leg cuffs 62 may be either elasticized or non elasticized and are preferably elasticized. Although described herein as being attached to the completed chassis or to the topsheet 38, one skilled in the art will appreciate that the leg cuffs 62 can also be attached to the back sheet 42. At this point, the barrier leg cuffs 62 are joined to the topsheet 38 by their proximal edges 64. They can be attached by any conventional means such as adhesives, heat/pressure sealing, ultrasonic bonding, or any other means or methods as are known in the art.

Once the leg cuffs 62 have been attached to the topsheet 38, a bonding agent is applied at station 220. The bonding agent is applied in the first waist region 22 as illustrated in FIG. 3. As illustrated in FIGS. 2 and 4, the bonding agent is applied at station 220 in the second waist region 24 of the diaper. In the embodiment described in FIG. 5, the bonding agent is applied to both the first waist region 22 and the second waist region 24 at station 220. As previously described, this bonding agent can be any bonding agent commonly used in the an including, but not limited to, adhesive tape, heat sealing, pressure sealing, ultrasonic bonding or a spot adhesive and is, preferably, a spot adhesive.

Once the bonding agent has been applied to the diaper 20, at station 230 the leg cuffs 62 are attached to the top sheet 38 with the cuffs 62 either directed outwardly from the longitudinal centerline 36 in the second waist region 24, as described in FIGS. 2 and 4 or directed inwardly of the longitudinal centerline 36 in the first waist region 22 as described in FIG. 3. In the embodiment depicted in FIG. 5, the leg cuffs 62 will either be attached to the topsheet 38 with the distal edges 64 directed toward the longitudinal centerline 36 in both the first waist region 22 and the second waist region 24 or with the distal edges 64 of both leg cuffs 62 directly outwardly of the longitudinal centerline 36 in both the first waist region 22 and the second waist region 24. One skilled in the art will appreciate that if the bonding agent is heat sealing, pressure sealing, ultrasonic bonding or a similar method, that station 220 and 230 may either be combined into one station or switched in their order in the process.

If the web 200 is not a chassis, and is either a topsheet 38 or backsheet 42, the chassis is formed at station 240. At this point, the top sheet 38 is associated with the absorbent core 44 and the backsheet 42, as described above. Once associated, the topsheet 38, backsheet 42 and absorbent core 44 form a completed chassis. The three elements, topsheet 38, backsheet 42, and absorbent core 44, are combined at station 240 from separate webs of each or from any combination of the three.

Once the chassis has been assembled, the leg notches are cut at station 250.

Having cut the leg notches, a bonding agent is applied in the waist region of the diaper 20, opposite to that region in which the bonding agent was applied at station 220, at station 260. For the embodiment described in FIGS. 2 and 4, the bonding agent is applied in the first waist region 22 of the diaper 20. For the embodiment described in FIG. 3, the bonding agent is applied in the second waist region 24 of the diaper. Finally for the embodiment described in FIG. 5, the bonding agent is provided on the proximal half of the inboard side of the barrier leg cuff 62 in the crotch region 26. Again, this bonding agent can be any bonding agent commonly used in the art including, but not limited to, adhesive tape, heat sealing, pressure sealing, ultrasonic bonding or a spot adhesive and is, preferably, a spot adhesive.

After the bonding agent has been applied at station 260, the diapers are folded at station 270 so that the bonding agent applied at station 260 joins the leg cuffs to the topsheet 38 in the proper position. At station 270 the diapers may either be C-folded or Z-folded, with Z-folding being preferred. In the process described in FIGS. 2 and 4, when the diaper is folded, the bonding agent contacts the leg cuffs 62 in the first waist region 22 of the diaper 20 to secure it to the topsheet 38 directed inwardly toward the longitudinal centerline 36. As illustrated in FIG. 3, the diaper is folded so that the leg cuffs 62 become joined to the topsheet 38 directed outwardly of the longitudinal centerline 36 in the second waist region 24 of the diaper 20. For the embodiment described in FIG. 5, the diaper 20 is folded so that the leg cuffs 62 becomes secured to the diaper 20 in the crotch region 26 providing a partial standup barrier in the crotch region 26. One skilled in the art will appreciate that if the bonding agent is heat sealing, pressure sealing, ultrasonic bonding or a similar method, stations 260 and 270 may either be combined into one station or switched in their order in the process.

To avoid any cross machine direction complications, the consumer technically completes the construction of the diaper 20. When ready to use the diaper 20 after purchase, the consumer opens the diaper 20 to a position in which the barrier leg cuffs 62 are attached in the first waist region 22 of the diaper 20 with their distal edges 66 directed inwardly toward the longitudinal centerline 36 and in which the distal edges 66 are directed outwardly of the longitudinal centerline in the second waist region 24, for the embodiments described in FIGS. 2–4. For the embodiment described in FIG. 5, the consumer opens the article to a position in which the barrier leg cuffs 62 have their distal edges 66 directed either inwardly toward the longitudinal centerline 36 in both waist regions, 22 and 24, or directed outwardly of the longitudinal centerline 36 in both waist regions, 22 and 24, and in which the diaper 20 has a partial standup barrier in the crotch region 26.

As a final step, the web 200 is cut into individual diapers.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a wearable, absorbent article having a longitudinal centerline comprising:

(a) providing a topsheet of indefinite length for an absorbent article, the topsheet having a first waist region, a second waist region and a crotch region located between the first waist region and the second waist region;

(b) attaching a pair of longitudinally extending barrier leg cuffs to the topsheet, each of the barrier leg cuffs having a proximal portion fixed to the topsheet and a distal portion unsecured at least to a portion of the topsheet;

(c) attaching the barrier leg cuffs to the topsheet in the second waist region, thus causing the distal portions of the leg cuffs to be attached directed outwardly from a longitudinal centerline of the topsheet; (d) associating the topsheet with a backsheet and a centrally positioned absorbent core to form a chassis; (e) cutting leg notches in a crotch region of the chassis; (f) folding the chassis so that the distal portions of the barrier leg cuffs are directed inwardly toward the longitudinal center line in the first waist region and attaching the barrier leg cuffs in the directed inward position; and (g) cutting the chassis transversely into individual articles.

2. The method of claim 1 wherein the attaching is performed by the method selected from the group consisting of adhesive bonding heat sealing, pressure sealing, and ultrasonic bonding.

3. The method of claim 1 wherein the attaching is performed with a spot adhesive.

4. The method of claim 1 wherein the attaching is provided on a side, farthest from the longitudinal centerline, of the leg cuff in the second waist region of the topsheet.

5. The method of claim 1 wherein the attaching is provided on a side, closest to the longitudinal centerline, of the leg cuff in the first waist region of the article.

\* \* \* \* \*

UNITED STATES PATENT AND TRADEMARK OFFICE
CERTIFICATE OF CORRECTION

PATENT NO.  : 5,565,050
DATED       : October 15, 1996
INVENTOR(S) : David M. Sageser and Mark D. Midkiff It is certified that error appears in the above-indentified patent and that said Letters Patent is hereby corrected as shown below:

On the title page, item [75], delete "Stanley G. Juergens, both of"

Col. 16, claim 2, line 19, after "bonding" insert --,--.

Col. 16, claim 3, line 21, replace "1" with --2--.

Signed and Sealed this

Twenty-fourth Day of December, 1996

Attest:

BRUCE LEHMAN

*Attesting Officer*  *Commissioner of Patents and Trademarks*